(12) United States Patent
Zöller et al.

(10) Patent No.: US 10,012,595 B2
(45) Date of Patent: Jul. 3, 2018

(54) TEST GLASS CHANGING

(75) Inventors: Alfons Zöller, Bad Soden-Salmunster (DE); Harro Hagedorn, Frankfurt am Main (DE); Eckhard Wirth, Gelnhausen (DE); Werner Weinrich, Langenselbold (DE); Tobias Gross, Garbsen (DE)

(73) Assignee: LEYBOLD OPTICS GMBH, Alzenau (DE)

( * ) Notice: Subject to any disclaimer, the term of this patent is extended or adjusted under 35 U.S.C. 154(b) by 1037 days.

(21) Appl. No.: 14/342,291

(22) PCT Filed: Jun. 28, 2012

(86) PCT No.: PCT/EP2012/002723
§ 371 (c)(1),
(2), (4) Date: Sep. 10, 2014

(87) PCT Pub. No.: WO2013/029707
PCT Pub. Date: Mar. 7, 2013

(65) Prior Publication Data
US 2014/0375986 A1    Dec. 25, 2014

(30) Foreign Application Priority Data

Sep. 2, 2011 (DE) .......... 10 2011 112 085
Jun. 1, 2012 (DE) .......... 10 2012 010 794

(51) Int. Cl.
*G01N 21/88* (2006.01)
*G01B 11/06* (2006.01)
(Continued)

(52) U.S. Cl.
CPC .......... *G01N 21/88* (2013.01); *G01B 11/0616* (2013.01); *G01B 11/0691* (2013.01); *G01N 21/253* (2013.01); *G01N 2021/8427* (2013.01)

(58) Field of Classification Search
CPC ... B65G 49/07; H01L 21/67742; H01L 21/68; H01L 21/68764; H01L 2224/75802; H01L 2224/80123; B81C 2203/054
See application file for complete search history.

(56) References Cited

U.S. PATENT DOCUMENTS 1,956,786 A * 5/1934 Bemis .............. B66C 1/36
  24/600.3
3,075,395 A * 1/1963 Leland ............. F15B 15/06
  384/604

(Continued)

FOREIGN PATENT DOCUMENTS

DE  10 2005 010 681 A1   9/2006
EP   0 241 589 A2   10/1987
(Continued)

OTHER PUBLICATIONS

Translation of the Notification of Reasons for Refusal (Type I Office Action), JP Patent Application No. 2014-527507, dated Aug. 3, 2015.

(Continued)

*Primary Examiner* — Tri Ton
*Assistant Examiner* — Rebecca C Bryant
(74) *Attorney, Agent, or Firm* — Mintz Levin Cohn Ferris Glovsky and Popeo, P.C.; John A. Bauer, Esq.

(57) ABSTRACT

A test glass changer for optically measuring layer properties in a vacuum coating system including a movable substrate holder for guiding a substrate through a stream of coating material; a mount connected to a rotary spindle and rotatable relative to the substrate holder about the rotary spindle; and a control device directing a test glass element into a ray path of an optical measuring device and into a stream of the coating material. The mount has at least two recesses offset eccentrically with respect to the spindle for one test glass element in each case. The control device can induce a (Continued)

rotational movement of the mount about the spindle. The centering device can exert a torque and holding moment on the mount to bring a test glass element arranged in one of the recesses into a measuring position of the measuring device. Related methods are also provided.

15 Claims, 8 Drawing Sheets

(51) Int. Cl.
*G01N 21/25* (2006.01)
*G01N 21/84* (2006.01)

(56) References Cited

U.S. PATENT DOCUMENTS

| | | | | |
|---|---|---|---|---|
| 4,108,762 | A | * | 8/1978 | Babunovic ............... B07C 5/122 198/377.1 |
| 4,455,501 | A | * | 6/1984 | Tojo .................... G03F 7/70691 310/328 |
| 4,828,391 | A | | 5/1989 | Zultzke et al. |
| 9,157,147 | B2 | * | 10/2015 | Scherer ................. C23C 14/547 |
| 2002/0176097 | A1 | | 11/2002 | Rodgers |
| 2007/0041091 | A1 | | 2/2007 | Takeuchi |
| 2011/0147610 | A1 | | 6/2011 | Macioszek et al. |
| 2011/0265583 | A1 | * | 11/2011 | Scherer ................. C23C 14/547 73/864.91 |

FOREIGN PATENT DOCUMENTS

| | | |
|---|---|---|
| EP | 0 241 589 B1 | 8/1991 |
| EP | 1493838 A1 | 1/2005 |
| JP | H 02110668 U | 9/1990 |
| TW | 200305875A A | 11/2003 |
| TW | 200641159 A | 12/2006 |

OTHER PUBLICATIONS

International Search Report of PCT/EP2012/002723 dated Nov. 15, 2012.

* cited by examiner

TEST GLASS CHANGING

CROSS-REFERENCES TO RELATED APPLICATIONS

This application is a 35 U.S.C. § 371 national stage entry of PCT/EP2012/002723, which has an international filing date of Jun. 28, 2012 and claims priority to German Patent Application No. 10 2011 112 085.1, filed on Sep. 2, 2011 and German Patent Application No. 10 2012 010 794.3, filed on Jun. 1, 2012. The contents of each of the above applications are hereby incorporated herein in their entireties by reference.

The present invention relates to test glass changing with the optical measurement of layer properties in vacuum coating systems according to the preambles of the independent patent claims.

A measuring arrangement for the optical monitoring of coating processes is known from DE 10 2005 010 681 A1. This measuring arrangement has a high measurement accuracy for transmission measurements of substrates or monitor glasses which are arranged on mobile substrate holders. Here, the light source is arranged within the vacuum chamber between a substrate holder and a diaphragm arranged beneath the substrate holder. The light receiver unit is arranged outside the vacuum chamber in the ray path of the light source. The substrate holder is designed to receive at least one substrate and can move in the vacuum chamber over a coating source. The substrate holder preferably rotates about an axis, wherein the at least one substrate crosses the ray path between the light source and the light receiver unit for transmission measurement purposes, and the diaphragm shades a measuring region over the coating source.

With this measuring arrangement, the transmission of a selected substrate or monitor glass on the rotating substrate holder is measured intermittently. With coating processes with a very high number of layers, it has been found in practice that fault accumulations may lead to considerable layer thickness faults. In order to eliminate such fault accumulations, it is often advantageous to change the measuring glass for an uncoated glass after a certain number of layers. In many layer systems, a change is necessary after approximately 30 to 40 layers. With the described measuring arrangement, the monitor glass can be changed manually only if the vacuum chamber is opened. This manual change leads to time-consuming process interruptions. Furthermore, the substrates may be contaminated by particles as a result of the opening and ventilation and the subsequent renewed evacuation. Even with additional cleaning steps, it has been found in practice that particle contamination is much greater than in processes without process interruptions of this type.

Further, EP 0 241 589 B1 discloses a test glass changer of the type mentioned in the introduction, in which a mount for receiving a plurality of test glasses is mounted on a substrate holder and is movable therewith and movable per se relative to the substrate. The described test glass changer comprises a control device, suitable for operation under vacuum, for introducing one test glass at a time into a ray path of a measuring apparatus and at least one stream of a coating material.

It was possible with this test glass changer to overcome a disadvantage of the prior art since test glasses can be changed under vacuum without ventilation of the vacuum chamber. Disadvantages have been found however even with this test glass changer. In particular, a protrusion of the mount from a switching finger has to be blocked exactly until a previously calculated angle of rotation of the mount is reached. The necessary angle of rotation is [360°/number of test glasses]. Furthermore, it must be ensured that a test glass, after passing through the angle of rotation, is arranged exactly in the center in the ray path of the optical measurement. A very precise mechanical coordination of the switching finger and of the protrusions is necessary for this purpose. The progression over time also has to be coordinated very accurately. It has been found in practice that the exact centering and the very precise mechanical coordination can only be achieved with difficulty, which leads to inaccurate and consequently non-reproducible positionings of the test glasses. Due to the rotation of the substrate holder during the coating, the mount with the test glasses can be easily moved, which additionally leads to an undesirable displacement of the test glass position.

The object of the invention is therefore to improve a test glass changing of the type described in the introduction.

This object is achieved by the features of the independent claims. Advantageous developments of the test glass changer are defined in the dependent claims.

The test glass changer according to the invention for optically measuring layer properties in vacuum coating systems which have a movable substrate holder for guiding at least one substrate on a path through at least one stream of a coating material, having a plate-like mount, which is rigidly connected to a rotary spindle and which is rotatable relative to the substrate holder about the rotary spindle, for test glass elements, and having a control device for introducing one test glass element at a time into a ray path of an optical measuring device and into the at least one stream of the coating material, wherein the mount has at least one recess offset eccentrically with respect to the spindle for each test glass element, and a rotational movement of the mount about the spindle can be induced by the control device, is characterized in that a centering device is provided, by means of which a torque and holding moment can be exerted on the mount in order to bring a test glass element arranged in one of the recesses into a measuring position of the measuring device. Accurate positioning of the test glass element for coating with the coating material and for execution of the measurement thereon is therefore possible in a simple manner without ventilating the vacuum chamber in order to change and/or position the test glass element and without having to mechanically coordinate various components in a very precise manner for positioning purposes.

Here, the test glass element may be a circular or oval test glass in particular. Further, the test glass element can be formed as a glass ring part which extends over a sector of a circle.

An embodiment is characterized in that the centering device has at least one actuator element arranged at a fixed angle to the substrate holder and at least one bearing element which is arranged at a fixed angle to the rotary spindle and can be acted on by the actuator element with spring force. As the actuator element engages with the bearing element, the plate-shaped mount connected fixedly to the rotary spindle and therefore the respective test glass element may then be positioned exactly, since the actuator element exerts, via the bearing element, a holding moment on the rotary spindle with the mount, such that the mount is fixed in its position relative to the substrate holder at least until the mount is rotated further as scheduled.

In a further embodiment a carrier plate that can be fastened or is fastened to the substrate holder and has a feedthrough for the rotary spindle and at least one measurement opening arranged eccentrically with respect to the rotary spindle may be provided, wherein the mount is arranged in a space between the substrate holder and the carrier plate.

The carrier plate in this embodiment is used inter alia to receive the actuator element, carries this therefore and fixes it at a fixed angle with respect to the substrate holder. The actuator element can thus engage with the bearing element on the rotary spindle leading through the carrier plate and can produce an accurate positioning. Further, the eccentric measurement opening releases only a ray path for the measurement, whereas any further test glass elements provided are protected by the carrier plate from the region of the vacuum chamber above the carrier plate.

A further embodiment is characterized in that the bearing element is formed as a hub which is connected rigidly to the rotary spindle and has a number V of indentations arranged on the periphery of the hub, wherein at least one of the indentations corresponds to one of the recesses, and wherein the actuator element is formed as a spring pin, which is arranged on the carrier plate and which can engage with one of the indentations via a free end with spring force.

An alternative embodiment is characterized in that the bearing element is formed as a trough-like indentation arranged in the plate-like mount, wherein the indentation corresponds to one of the recesses, and in that the actuator element comprises a ball element, an upper stop opening, arranged in the carrier plate, of the ball element that can be arranged or is arranged between the plate-like mount and the carrier plate, and a spring element which is arranged on the carrier plate and acts on the ball element, wherein the ball element can engage with the indentation with spring force.

Both alternatives have the advantage that, due to the engagement of the spring pin or of the ball element with one of the corresponding indentations, positioning can be very exact, in particular if the radii of the spring pin end or of the ball element are coordinated with the radii of the corresponding indentations, such that the spring pin or the ball element engages with the corresponding indentation substantially without play.

In accordance with a further embodiment the control device comprises a number of rotary arms or protrusions, of which the number corresponds to the number of recesses. A torque can be applied to the rotary spindle by means of the rotary arms or protrusions. Further, switching fingers that can be moved into the respective orbital path of the rotary arms or protrusions are provided, such that the mount is rotatable by an angular distance by means of the rotary arms or protrusions.

Since the number of rotary arms or protrusions corresponds to the recesses, of which the number in turn preferably corresponds to the number of test glass elements arranged in the mount, a further test glass can be easily and efficiently rotated into the measuring position as a result of the engagement of the switching finger with one of the rotary arms or protrusions, without the need to carry out a complex mechanical coordination. It may even be sufficient to move the switching finger only for a short period of time into the orbital path of the rotary arms or protrusions in order to entrain a rotary arm or a protrusion.

A protective device for protecting against influences from the region of the vacuum chamber beneath the substrate support is arranged between the mount and the substrate holder, such that only one single test glass element at a time is exposed in its coating and measuring position. It is preferable for a protective device to be arranged on the carrier plate, such that only one single test glass element at a time is exposed in its coating and measuring position.

Here, the protective device may be in particular a circular plate which is arranged coaxially with the rotary spindle and which has a single opening that can be brought into alignment with the measuring position.

The protective device, in particular in the form of a circular plate, provides simple yet effective protection against a coating process for the mount, including the movable parts thereof, and the test glass elements not intended for coating. The protective device releases only the coating of the test glass element in the measuring position.

Besides the above-mentioned transmission measurement, the layer properties on the test glass elements can also be measured in reflection. In the case of the reflection measurement, the carrier plate may be formed without an opening.

The method according to the invention for test glass changing by means of a device of the previously described type is characterized in that, before a test glass element arranged in one of the recesses is brought into a measuring position of the measuring device, a rotational movement of the mount is induced by means of the control device, said rotational movement bringing said test glass element into a first position, of which the angular distance from the measuring position is smaller than the angular distance between the recesses, and said test glass element is then brought into the measuring position by means of the centering device.

Further objectives, features, advantages and possible applications will become clear from the description of preferred exemplary embodiments of the invention with reference to the accompanying drawings. Here, all features described and/or illustrated schematically form part of the subject matter of the invention both individually and in any combination, irrespective of their summary in the claims or the dependency references of the claims.

Figure 1:
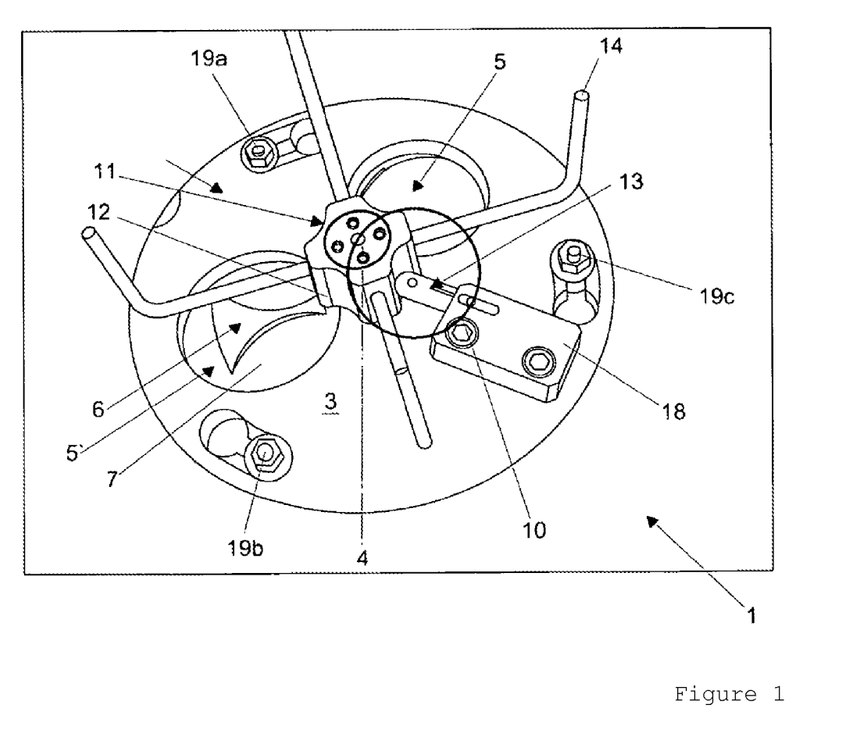
FIG. 1 shows a test glass changer in accordance with an embodiment of the invention with a hub in a first position with respect to a spring pin.

A preferred embodiment of the test glass changer 1 is illustrated in FIG. 1. Hereinafter, the side of the test glass changer visible in FIG. 1 will be referred to as the upper side and the side not visible will be referred to as the lower side, although the subject matter of the invention is not to be limited hereby.

A carrier plate 3, which is circular in the present embodiment, has a feedthrough (not visible in FIG. 1) in its center, through which a rotary spindle 4 is guided.

A mount 6 for receiving test glass elements is provided beneath the carrier plate 3. The test glass elements may be formed in a circular or oval manner or as a glass ring part. The carrier plate 3 in the present embodiment has an opening 5', which is arranged eccentrically and through which test glass elements can be inserted into or removed from the mount 6.

In the present embodiment the mount 6 has four openings 7 for receiving the test glass elements. The mount 6 is formed in this embodiment as a circular plate and is connected rigidly at its center to the rotary spindle 4. The mount 6 is mounted jointly with the rotary spindle 4 and the hub 11 so as to be rotatable with respect to the carrier plate 3.

The openings 7 in the mount 6 can be formed as circular bores, of which the maximum diameter is slightly smaller than the diameter of the used test glass elements. In particular, the bores are formed as blind bores. Due to the difference between the radii, a bearing edge of the test glass element is produced on the opening 7 in the mount 6.

The centering device has at least one actuator element (control element) arranged at a fixed angle to the substrate holder and at least one bearing element which is arranged at a fixed angle to the axis of rotation and which can be acted on by the actuator element, preferably with spring force. Here, spring force is understood to mean any force induced by a resilient element, in particular a clamping force of a spring.

A hub 11 is arranged on the upper side of the carrier plate 3 as a bearing element and is fixedly connected to the rotary spindle 4. The hub 11 is rotatable together with the rotary spindle 4 with respect to the carrier plate 3. The hub 11, on its periphery, comprises four indentations 12 running in the axial direction, with which a movable spring pin 13 as an actuator element engages. The hub 11 with the indentations 12 and the spring pin 13 together form the centering device 10.

Rotary arms 14 are provided on the ridges of the hub 11 between the indentations 12 and initially extend radially outwardly parallel to the carrier plate 3 in order to then bend upwardly at an angle of approximately 90° in the region of the radially outermost edge of the carrier plate 3. The rotary arms can also be attached to the rotary spindle 4.

The spring pin 13 is mounted in a spring pin bearing 18, which enables a movement of the spring pin 13 in the radial direction of the rotary spindle 4. The bearing 18 is connected fixedly, yet preferably removably, to the carrier plate 3. In the present case, the bearing 18 is formed as a cylinder block and is screwed to the carrier plate 3. As the hub 11 rotates, the spring pin 13 is pressed out from the indentation 12 against the spring force and over the ridge of the hub 11 between two indentations 12.

Figure 2:
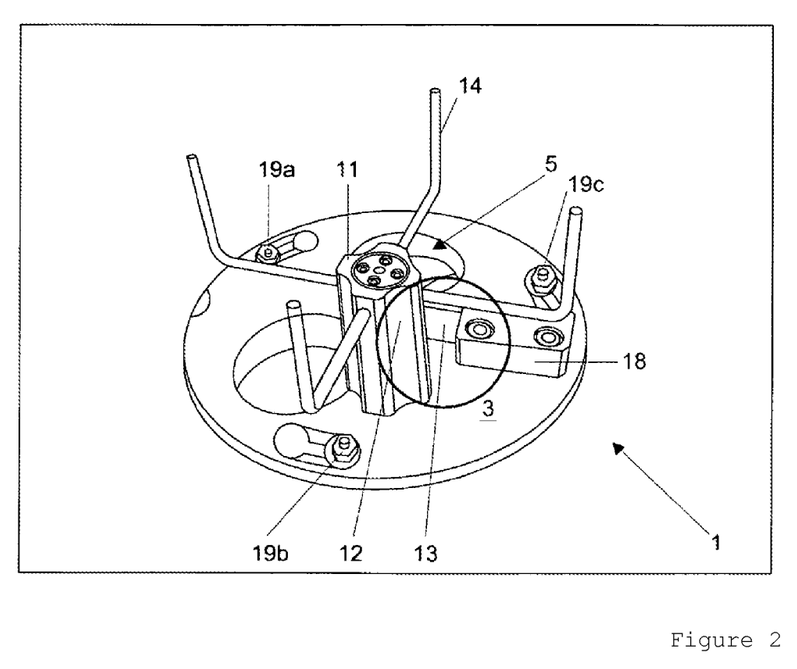
FIG. 2 shows the test glass changer illustrated in FIG. 1 with a hub in a second position with respect to a spring pin.

In FIG. 2 the hub 11 is shown in its position relative to the spring pin 13 in which said spring pin is arranged in the middle between two indentations 12 and with the maximum distance between rotary spindle 4 and spring pin 13. If the rotary spindle 4 is now rotated slightly with respect to the carrier plate 3 by the movement of the rotary arms 14, the spring pin 13 runs as a result of its spring force into the next indentation 12 and is positioned exactly in the center of this indentation 12. Provided no torque is applied, the hub 11 and therefore the mount 6 with the test glass elements are held in their position by the spring force of the spring pin 13.

The carrier plate 3 in the present embodiment has a further opening 5, which is arranged eccentrically and which lies in a ray path, for example for transmission measurements.

The carrier plate 3 is connected fixedly to the substrate holder 2, in this embodiment by means of the screws 19*a*, 19*b*, 19*c*, which fasten the carrier plate 3 in the manner of a bayonet closure.

Figure 3:
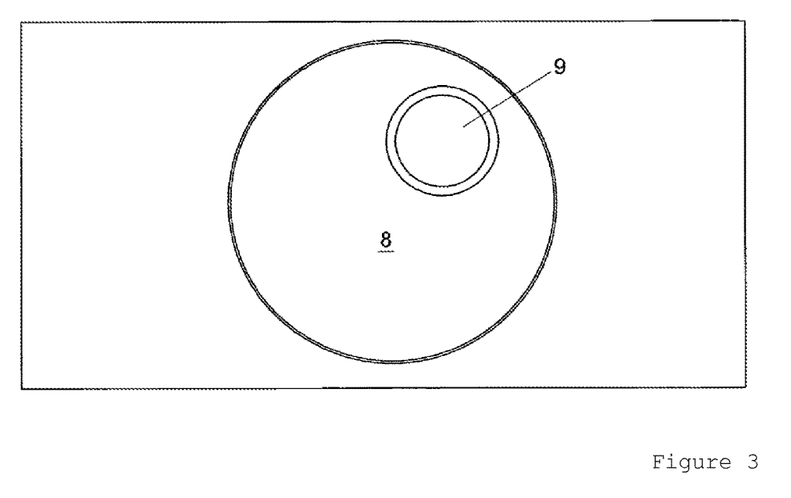
FIG. 3 shows a cover plate for a test glass changer in accordance with an embodiment of the invention.

FIG. 3 shows a cover plate 8, which is fastened or can be fastened to the lower side of the carrier plate 3. Here, the fastening of the cover plate 8 to the carrier plate 3 leaves enough space for the rotation of the mount 6 with the test glass elements. The cover plate 8 has an opening 9, which is positioned in the radial direction such that it is aligned with the opening 5 in the carrier plate 3. Due to the positioning of the opening 7 in the mount 6 by means of the indentations 12 in the hub 11 and the spring pin 13, the respective test glass is positioned exactly in the opening 5 of the carrier plate 3 and the opening 9 in the cover plate 8.

In a further embodiment a carrier plate, cover plate and a cover are interconnected by means of the screws and form a unit that can be fitted onto the calotte in a preassembled manner.

Figure 4:
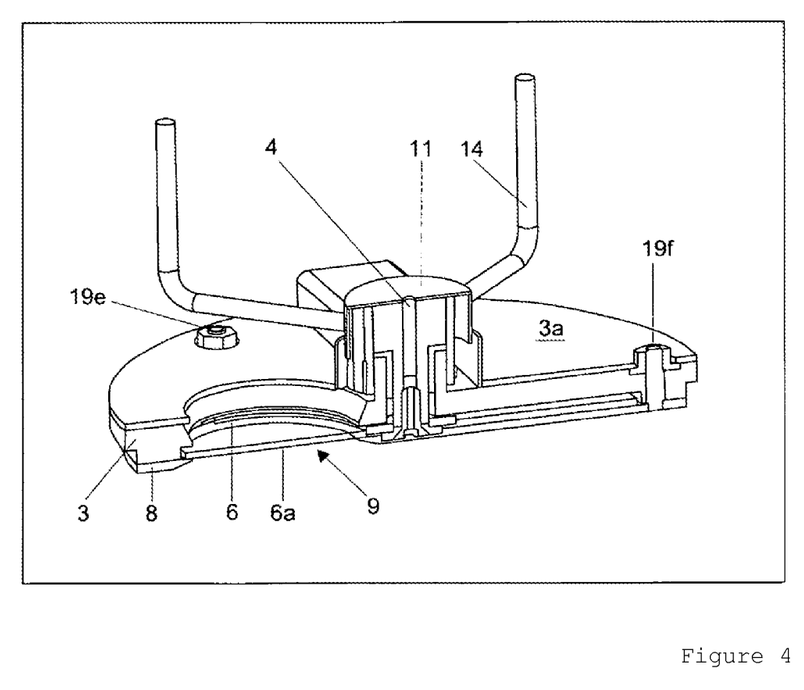
FIG. 4 shows some components of a further embodiment of a test glass changer according to the invention.

FIG. 4, in an embodiment of the test glass changer according to the invention, shows a carrier plate 3 with a cover 3*a* arranged thereon. A cover plate 8, which, similarly to the embodiment of FIG. 3, has an opening 9, through which a test glass 6 *a* can be coated from beneath, is arranged beneath the carrier plate 3 as a protective device. The cover plate 8 is connected by means of screws 19 *e*, 19 *f* to the lower face of the carrier plate 3, wherein the mount 6 can be moved between the cover plate 8 and carrier plate 3.

In the illustrated embodiments the substrates and therefore the test glass elements are coated from beneath. The cover plate 8, by means of its one opening 9, delimits the coating to precisely the test glass that is positioned in the openings 5 and 9. Due to this arrangement of the opening 5 in the carrier plate 3, the opening 7 in the mount 6 with the test glass, and the opening 9 in the cover plate 8, the ray path is released for the transmission measurement of the current test glass element.

In order to bring a new test glass into the stream of the coating material and also into the ray path for the transmission measurement, the mount 6 is rotated with respect to the carrier plate 3 and the cover plate 8 by means of the rotary arms 14, the hub 11 and the rotary spindle 4, and positions the carrier glass arranged next in the mount 6 over a circular path.

Figure 5:
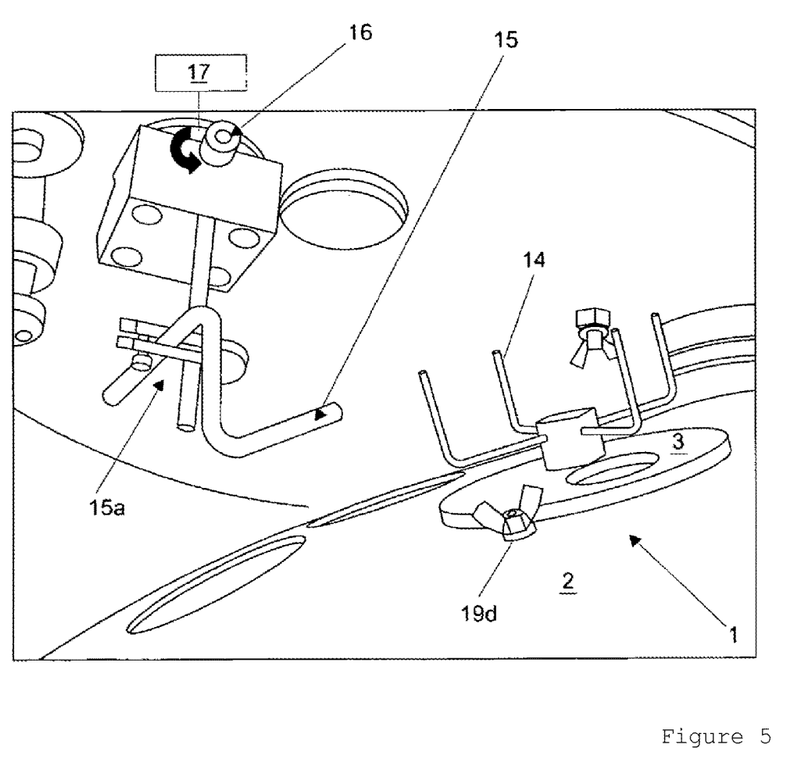
FIG. 5 shows the arrangement of a test glass changer in accordance with an embodiment of the invention on a substrate holder in relation to a switching device with a switching finger in a first operating position.

FIG. 5 shows the arrangement of the test glass changer 1 on the substrate holder 2, which in this embodiment is formed as a rotatable calotte. The test glass changer 1 is screwed in a corresponding opening to the calotte by means of a screw 19*d*. Here, the lower side of the test glass changer 1, that is to say the cover plate 8, points toward the interior of the calotte.

The hub 11 with the rotary arms 14 is arranged on the outer face of the calotte.

Independently of the calotte, a switching device is provided in relation to the test glass changer 1 and consists of a switching finger 15, which is connected via a shaft 16 to an actuator 17, whereby the switching finger 15 can be driven. Due to the movement of the shaft 16, the switching finger 15 can be pivoted in the direction of the test glass changer 1. A hinge device 15*a* is arranged on the shaft 16 in order to adjust the switching finger 15.

Figure 6:
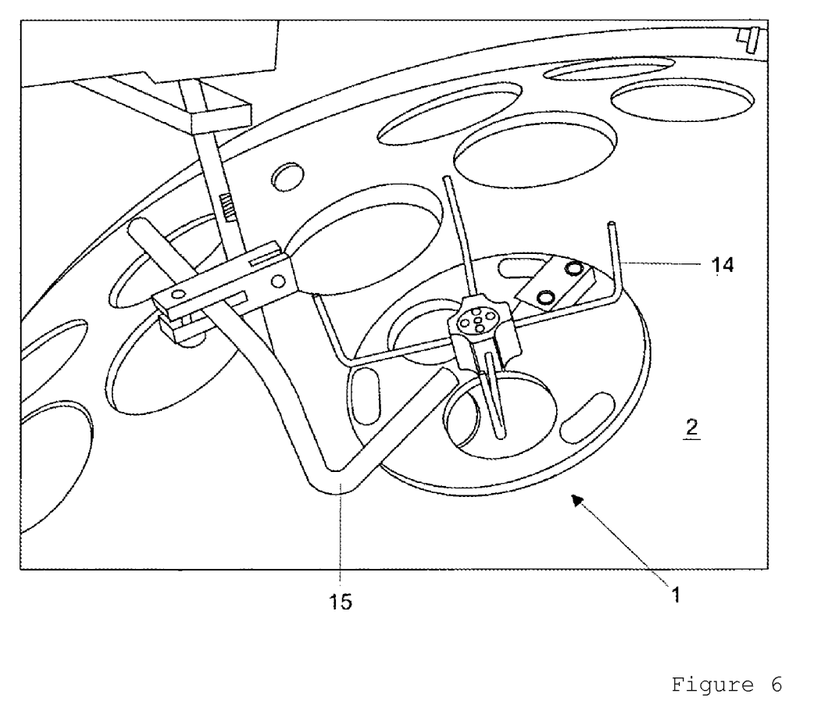
FIG. 6 shows the arrangement illustrated in FIG. 5 with the switching finger in a second operating position.

As is shown in FIG. 6, the switching finger 15 is located, once pivoted, between two rotary arms 14 of the test glass changer 1. If the calotte is now rotated during the coating process, one of the rotary arms 14 comes into contact with the switching finger 15, such that a rotation of the hub 11 with the rotary spindle 4 is triggered by the rotation of the calotte. The mount 6 with the test glass elements is therefore rotated with respect to the components connected to the calotte for conjoint rotation, that is to say the carrier plate 3 and cover plate 8.

If, as a result of the rotation of the calotte, the hub 11 is rotated so far that the spring pin 13 has exceeded the point of maximum distance between the rotary spindle 4 and spring pin 13, the switching finger 15 is pivoted back by the action of the actuator 17 via a rotation of the shaft 16. The spring force of the spring pin 13 leads to the exact positioning of the hub 11 and therefore to the precise centering of the next test glass element in the aligned openings 5, 7 and 9.

In the present embodiment the shaft 16 is guided outwardly through a vacuum feedthrough from the vacuum coating chamber, where the actuator 17 is arranged. The shaft 16 can be moved easily manually or in a motor-driven manner through the vacuum feedthrough.

Of course, further embodiments of a drive of the switching finger 15 are also included by the invention.

In particular, a pivot drive of the switching finger 15 may have a rotary spindle with an orientation different from that illustrated in FIG. 5.

To rotate the calotte, the rotary drive provided and not illustrated in the figure is used. The calotte is preferably rotated more slowly during the test glass change than during a regular coating process. In particular, the changing process can be automated very easily with the aid of an angle sensor, which is coupled to the rotary drive of the calotte.

Alternatively to the foregoing, it is also possible to rotate the rotary arms 14 if the calotte is stationary. To this end, the switching finger 15, in order to be pivoted in between two rotary arms 14, has to be additionally mechanically rotated in order to guide the switching finger 15 so far that the spring pin 13 is guided into the next indentation 12.

The test glass changer 1 according to the invention, due to the self-centering with the aid of the spring pin 13, enables an exact positioning of a test glass element in the stream of the coating material and/or in the ray path of the transmission measurement. Compared with the prior art, it is also possible to change the test glass elements when the substrate holders are stationary.

Figure 7:
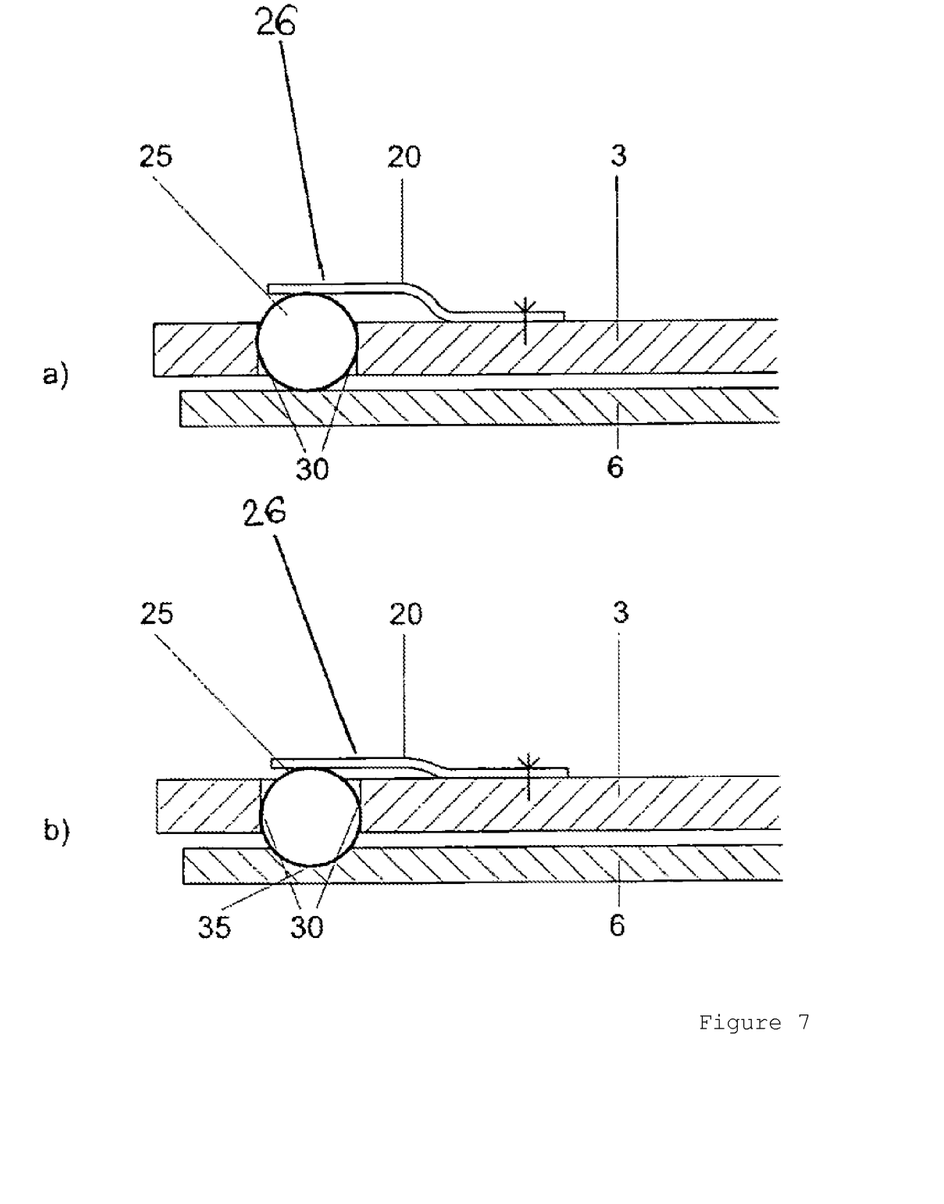
FIGS. 7*a*-7*b* show an actuator element and a bearing element of a further embodiment of the invention.

Alternatively to the positioning with spring pin and hub, an actuator element and bearing element may also be formed as illustrated in FIGS. 7a-7b.

A leaf spring 20 is fixed at one end on the carrier plate 3. A ball 25 is located between the carrier plate 3 and mount 6 for the test glass element. The carrier plate 3 is provided with a circular stop opening 30, which is formed in such a way that the ball 25 has an upper stop. The ball 25 is pressed downwardly onto the mount 6 by means of spring force; see FIG. 7a, which shows the arrangement during a changing process with unpositioned test glass.

The mount 6 for the test glass elements is provided with trough-like indentations 35 (hollows), which are arranged such that the ball 25 is pressed into one of the hollows 35 if a test glass is located in the measuring position, see FIG. 7b. Due to the spring pressure on the ball 25, the holding plate 6 is stopped and fixed. For the next change, the holding plate 6 is rotated via the rotary spindle by a rotary arm with a force which overcomes the spring force. The hollow 35 leaves the region of the ball 25 and the holding plate 6 pushes the ball 25 upwardly, as illustrated in FIG. 7a.

Figure 8:
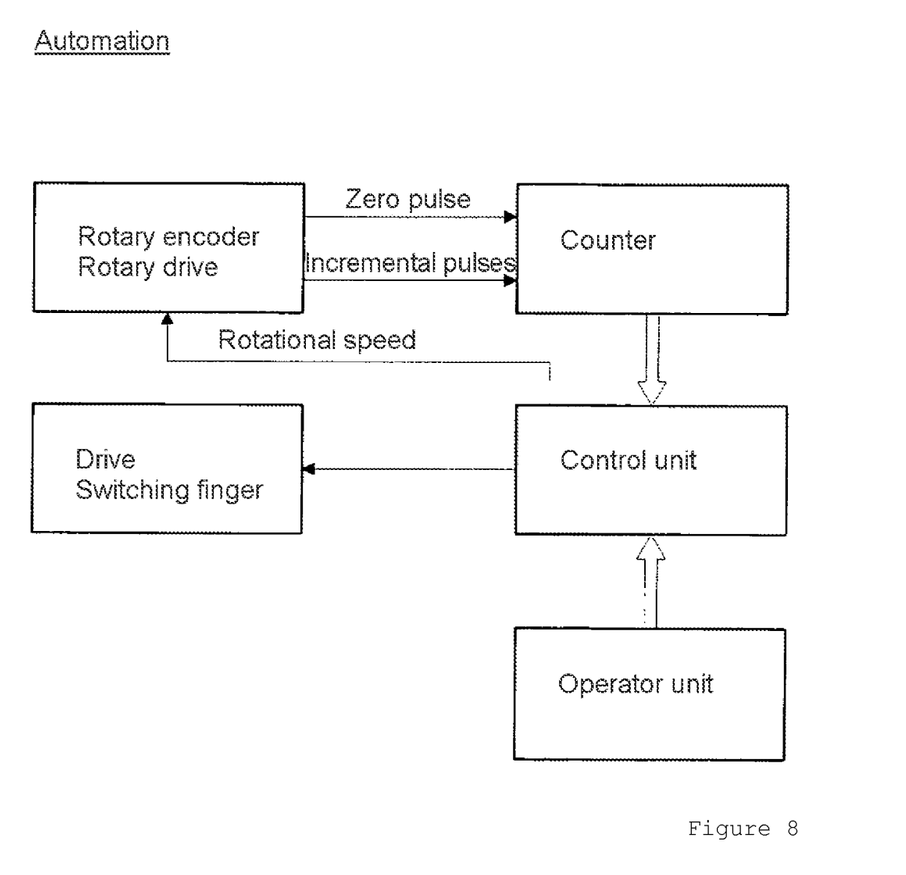
FIG. 8 shows a block diagram of an automated process for test glass changing.

The course of a test glass change is illustrated in FIG. 8.

A rotary encoder is rigidly coupled without slip to the rotary spindle of the substrate holder 2 (for example calotte, flat plate).

The rotary encoder, with each revolution, delivers a zero pulse always at the same rotary angle. Furthermore, a fixedly defined number of incremental pulses per rotary angle are generated during the rotation. A rotary encoder with 8192 pulses per revolution is preferably used. This corresponds to a resolution of one pulse per 2.6 angular minutes.

The zero pulse is transmitted via a line to a counter. The incremental pulses are transmitted via a second line to the counter. The counter is reset with the zero pulse and is incremented by the incremental pulses. The counter state thus corresponds to a certain rotary angle of the substrate holder 2.

The current counter state is read out by a control unit. The current rotary angle of the substrate holder 2 relative to the zero pulse is therefore known. The position of the test glass changer 1 relative to the zero pulse can be established via a calibration. The current position of the test glass changer 1 during the rotation is therefore known.

The course of an automatic test glass change will be described hereinafter.

The substrate holder 2 is rotated by the drive. At a preprogrammed rotary angle, an output for activating the switching finger 15 is triggered by the control unit. The rotary angle for triggering the output is selected such that the switching finger 15 is pivoted in just before a rotary arm 14 of the changer 1 passes the switching finger 15.

At a further preprogrammed rotary angle, the output for the switching finger 15 is reset, such that the switching finger 15 is pivoted back again. This angle is selected such that the switching finger 15 passes precisely the point between two notches 12; see FIG. 1. In the variant with the ball fixing, the angle is selected such that the ball 25 enters precisely one hollow 35, see FIG. 7. The changing process is therefore completed.

The rotational speed of the drive for the substrate holder 2 can be controlled. The rotational speed can be adapted at any time during the changing process according to the rotary angle, such that on the one hand a secure positioning is implemented with minimal stressing of the mechanical components and on the other hand the process is completed as quickly as possible. The rotational speed can then be increased again.

Whereas the known systems in practice only function reliably in small sputtering systems with a rotary plate diameter of 550 mm, the test glass changer 1 according to the invention can also be used in large systems with a calotte diameter of 1500 mm and more, which have imprecise mechanics compared with small sputtering systems. Further, the test glass changer 1 according to the invention can be placed at practically any desired point on a substrate holder 2 (calotte, flat plate, planetary drive). In order to adapt existing systems, merely the switching device formed of switching finger 15, shaft 16 and actuator 17 has to be provided.

As a result, the principle of the present invention can also be applied to systems in which the coating is not performed from the inside out, but from above. In this case, the test glass changer 1 is rotated through 180°, such that the cover plate 8 points toward the outwardly or upwardly arranged coating source and the carrier plate 3 is arranged on the lower side of the substrate holder.

Besides the transmission measurement mentioned above, the layer properties on the test glass elements can also be measured in reflection. In the case of the reflection measurement, the support plate 3 can be formed without an opening 5.

LIST OF REFERENCE SIGNS 1 test glass changer
2 substrate holder 3 carrier plate
3a cover
4 rotary spindle
5 opening in the carrier plate 3
5' opening in the carrier plate 3
6 mount
6a test glass
7 receiving opening in the mount 6
8 cover plate
9 opening in the cover plate 8
10 centering device
11 bearing element, hub
12 indentation
13 actuator element, spring pin
14 rotary arm
15 switching finger
15a hinge device
16 shaft
17 actuator
18 spring pin mount
19a,b,c,d,f screws
20 spring
25 ball
26 actuator element
30 stop opening
35 bearing element, indentation

The invention claimed is:

1. A test glass changer, comprising:
a movable substrate holder for guiding at least one substrate on a path through at least one stream of a coating material;
a mount including at least one recess configured to receive a test glass element, wherein the mount is rigidly connected to a rotary spindle and is rotatable relative to the substrate holder about the rotary spindle, and wherein the recess is offset eccentrically with respect to the spindle;
a control device configured to rotate the mount about the spindle for introducing one of the at least one recess at a time into a ray path of an optical measuring device and into the at least one stream of the coating material; and
a centering device configured to exert a spring force on the mount in order to bias a test glass element received in one of the recesses into a centered position with respect to the ray path of the optical measuring device, the centering device including,
an actuator element arranged at a fixed angle to an angle of rotation; and
a bearing element which is arranged at a fixed angle to the rotary spindle and can be acted on by the actuator element with a spring force;
wherein the bearing element is formed as a hub connected rigidly to the rotary spindle and having a number of indentations arranged on the periphery of the hub;
wherein the actuator element is formed as a spring pin configured to engage with one of the indentations via a free end with a spring force; and
wherein at least one of the indentations corresponds to one of the at least one recesses of the mount.

2. The test glass changer as claimed in claim 1, further comprising a carrier plate that is fastened to the substrate holder and defining a space therebetween, the carrier plate including:
a feedthrough for the rotary spindle; and
at least one measurement opening arranged eccentrically with respect to the rotary spindle;
wherein the mount is positioned in the space between the substrate holder and the carrier plate.

3. The test glass changer as claimed in claim 1, wherein the control device comprises a number of rotary arms or protrusions, by means of which a torque can be applied to the rotary spindle, and has at least one switching finger which can be moved into the respective orbital path of the rotary arms or protrusions, wherein the mount is rotatable by an angular distance by means of the rotary arms or protrusions.

4. The test glass changer as claimed in claim 1, further comprising a protective device arranged between the mount and the substrate holder, such that only one single test glass element at a time is exposed in its coating and measuring position.

5. The test glass changer as claimed in claim 4, wherein the protective device is formed as a cover plate which has an opening that can be aligned with the measuring position.

6. The test glass changer as claimed in claim 1, wherein at least one test glass element is formed as a circular or oval test glass.

7. The test glass changer as claimed in claim 1, wherein at least one test glass element is formed as a glass ring part.

8. A method for test glass changing in a device as claimed in claim 1, the method comprising: before a test glass element arranged in one of the recesses is brought into a measuring position of the measuring device, inducing a rotational movement of the mount by means of the control device, said rotational movement brings the test glass element into a first position at which an angular distance from a measuring position is smaller than an angular distance between the recesses; and bringing the test glass element to a measuring position by means of the centering device.

9. A test glass changer, comprising:
a movable substrate holder for guiding at least one substrate on a path through at least one stream of a coating material;
a mount including at least one recess configured to receive a test glass element, wherein the mount is rigidly connected to a rotary spindle and is rotatable relative to the substrate holder about the rotary spindle, and wherein the recess is offset eccentrically with respect to the spindle;
a control device configured to rotate the mount about the spindle for introducing one of the at least one recess at a time into a ray path of an optical measuring device and into the at least one stream of the coating material;
a carrier plate that is fastened to the substrate holder and defining a space therebetween, the carrier plate including:
a feedthrough for the rotary spindle; and
at least one measurement opening arranged eccentrically with respect to the rotary spindle;
wherein the mount is positioned in the space between the substrate holder and the carrier plate;
a centering device configured to exert a spring force on the mount in order to bias a test glass element received in one of the recesses into a centered position with respect to the ray path of the optical measuring device, the centering device including:
an actuator element arranged at a fixed angle to an angle of rotation; and
a bearing element which is arranged at a fixed angle to the rotary spindle and can be acted on by the actuator element with a spring force, wherein the bearing element is formed as a trough-like indentation arranged in the mount, the indentation corresponding to one of the at least one recesses of the mount, and wherein the actuator element comprises:
- a ball element,
- an upper stop opening formed in the carrier plate and dimensioned to receive the ball element, and
- a leaf spring fixed at one end to the carrier plate and configured to exert the spring force on the ball element to cause the ball element to engage with the indentation.

10. The test glass changer as claimed in claim 9, wherein the control device comprises a number of rotary arms or protrusions, by means of which a torque can be applied to the rotary spindle, and has at least one switching finger which can be moved into the respective orbital path of the rotary arms or protrusions, wherein the mount is rotatable by an angular distance by means of the rotary arms or protrusions.

11. The test glass changer as claimed in claim 9, further comprising a protective device arranged between the mount and the substrate holder, such that only one single test glass element at a time is exposed in its coating and measuring position.

12. The test glass changer as claimed in claim 11, wherein the protective device is formed as a cover plate which has an opening that can be aligned with the measuring position.

13. The test glass changer as claimed in claim 9, wherein at least one test glass element is formed as a circular or oval test glass.

14. The test glass changer as claimed in claim 9, wherein at least one test glass element is formed as a glass ring part.

15. A method for test glass changing in a device as claimed in claim 9, the method comprising: before a test glass element arranged in one of the recesses is brought into a measuring position of the measuring device, inducing a rotational movement of the mount by means of the control device, said rotational movement brings the test glass element into a first position at which an angular distance from a measuring position is smaller than an angular distance between the recesses; and bringing the test glass element to a measuring position by means of the centering device.

* * * * *